(12) United States Patent
Wenk et al.

(10) Patent No.: US 8,227,399 B2
(45) Date of Patent: Jul. 24, 2012

(54) POLYGLYCEROL ESTERS AND THEIR USE

(75) Inventors: Hans Henning Wenk, Mülheim an der Ruhr (DE); Ulrike Kottke, Grossenhausen-Linsengericht (DE); Jennifer B. Ponder, Cincinnati, OH (US)

(73) Assignee: Evonik Goldschmidt GmbH, Essen (DE)

( * ) Notice: Subject to any disclaimer, the term of this patent is extended or adjusted under 35 U.S.C. 154(b) by 100 days.

(21) Appl. No.: 12/704,708

(22) Filed: Feb. 12, 2010

(65) Prior Publication Data

US 2011/0201538 A1    Aug. 18, 2011

(51) Int. Cl.
*C11D 3/20* (2006.01)

(52) U.S. Cl. ....................................... 510/505

(58) Field of Classification Search .................... 510/505
See application file for complete search history.

(56) References Cited

U.S. PATENT DOCUMENTS

| | | | |
|---|---|---|---|
| 4,214,038 A | 7/1980 | McCarty et al. | |
| 4,454,113 A * | 6/1984 | Hemker | 424/63 |
| 4,456,627 A * | 6/1984 | Van Heteren et al. | 426/603 |
| 4,690,774 A * | 9/1987 | Vishnupad et al. | 516/29 |
| 4,725,431 A * | 2/1988 | Hourihan et al. | 424/66 |
| 5,162,057 A * | 11/1992 | Akiyama et al. | 106/243 |
| 5,443,846 A * | 8/1995 | Yoshioka et al. | 424/498 |
| 5,585,506 A * | 12/1996 | Harvey et al. | 554/173 |
| 6,620,904 B2 | 9/2003 | Lemke | |
| 6,706,903 B1 * | 3/2004 | Hendree et al. | 554/211 |
| 7,550,170 B2 * | 6/2009 | Shiiba et al. | 426/605 |
| 2004/0175341 A1 * | 9/2004 | Manning | 424/70.11 |
| 2006/0276370 A1 | 12/2006 | Zhang et al. | |
| 2006/0292281 A1 * | 12/2006 | Kragh et al. | 426/565 |
| 2010/0021399 A1 * | 1/2010 | Rampoldi et al. | 424/59 |

FOREIGN PATENT DOCUMENTS

JP   3886310 B2   12/2006
WO   WO 2008/012220 A1 *  1/2008

OTHER PUBLICATIONS

Wikipedia definition of "polydispersity index". No date available.*
Cassel, S. et al., "Original synthesis of linear, branched and cyclic oligoglycerol standards", 2001 Eur. J. Org. Chem., pp. 875-896.

* cited by examiner

*Primary Examiner* — John Hardee
(74) *Attorney, Agent, or Firm* — Scully, Scott, Murphy & Presser, P.C.

(57) ABSTRACT

The present invention relates to polyglycerol partial esters of linear, unsubstituted carboxylic acids with the provisos that the polyglycerol obtained by hydrolysis or alcoholysis of the polyglycerol partial ester comprises an average degree of polymerization of from 2 to 8 and the polydispersity index of said polyglycerol is greater than 0.75.

6 Claims, No Drawings

POLYGLYCEROL ESTERS AND THEIR USE

FIELD OF THE INVENTION

The present invention relates to polyglycerol partial esters of linear, unsubstituted carboxylic acids with the provisos that the polyglycerol obtained by hydrolysis or alcoholysis of the polyglycerol partial ester comprises an average degree of polymerization of from 2 to 8 and the polydispersity index of said polyglycerol is greater than 0.75.

BACKGROUND OF THE INVENTION

Various uses for polyglycerol esters ("PGEs") are known. See, for example, U.S. Pat. No. 4,214,038 and US 2006/0276370. PGEs are esters typically obtained by reacting polyglycerol and a fatty acid. Polyglycerols may be prepared from glycerin as described in the literature, for example, as described in U.S. Pat. No. 6,620,904. In general, oligomerization of the glycerol unit is an intermolecular reaction between two glycerin molecules to form a diglycerol. Two such oligomers can also be reacted together, or an oligomer can be reacted with an additional glycerin to form yet higher oligomers. Polyglycerols may be converted to polyglycerol esters by typical esterification techniques for example, via reaction with fatty acids, fatty acid chlorides, and the like. The fatty acids used in the esterification can be a mixture of fatty acid chain lengths such as, for example, the fatty acid mixtures derived from coconut oil or tallow. The fatty acids may be saturated or unsaturated, and may contain from about 12 to about 22 carbon atoms, or about 10 to 22 carbon atoms. The fatty acid mixtures derived from natural fats and oils such as, for example, rapeseed oil, peanut oil, lard, tallow, coconut oil, soybean oil can be converted to saturated form by hydrogenation, such processes being readily understood by one of ordinary skill in the art.

Consumer fabric treatment compositions are often formulated to provide improved fabric feel. Such compositions can be formulated, for example, as liquid softening compositions, dryer sheets, or detergent formulations. Unfortunately, depending on the type of softening active used, existing fabric softening compositions can suffer from a variety of disadvantages. For example, currently used actives can be excessively expensive, may, impart a greasy feel to textiles, and in some cases may cause treated fabric to become hydrophobic. In addition, some softening agents, such as quaternary ammonium compounds, can be difficult to formulate with, particularly when combined with anionic surfactants as flocculation/precipitation may occur. Further, there is a need for fabric softening agents that may be used in low water or compacted formulations, in contrast to currently used fabric softening agents which may be difficult to formulate as low-water compositions.

The use of polyglycerol esters in fabric softening applications has been described for example in JP3886310 which claims a fiber softening agent comprising a mixture of polyglycerol fatty acid ester and sucrose fatty acid ester.

There still is a growing demand for fabric softening substances which can be produced easily on basis of renewable sources and which give an excellent feel to the fabric. It was an object of the invention to provide such fabric softening substances.

SUMMARY OF THE INVENTION

It has now been found, surprisingly, that the novel polyglycerol partial esters of claim 1 fulfill the requirements.

The present invention therefore relates to polyglycerol partial ester having the structure of Formula (I)

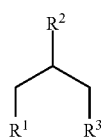

Formula (I)

with $R^1$, $R^2$ and $R^3$ independent from each other, equal or different selected from the group consisting of
- —OH,
- —$OR^4$, with $R^4$ a linear, unsubstituted acyl radical with a chain length of from 16 to 22 carbon atoms with the proviso that the monocarboxylic acids obtained from the acyl radical by saponification bears an iodine value of smaller than 50, preferred smaller than 30, more preferred about 1-25,
- —$OR^5$, with $R^5$ a radical having the structure of Formula (I) wherein one of $R^1$, $R^2$ and $R^3$ being a direct bond to the oxygen of —$OR^5$ wherein each molecule of the polyglycerol partial ester comprises at least one of each —$OR^4$ and —$OR^5$, with the provisos that the polyglycerol obtained by hydrolysis or alcoholysis of the polyglycerol partial ester comprises an average degree of polymerization of from 2 to 8 and the polydispersity index of said polyglycerol is greater than 0.75, preferably greater than 1.0, particularly preferred greater than 1.2, as specified below.

The invention further relates to methods for preparing the polyglycerol partial esters according to the invention. Yet the invention also relates to the use of the polyglycerol partial esters according to the invention in fabric softeners and fabric softeners comprising polyglycerol partial esters according to the invention.

An advantage of the present invention is that the polyglycerol partial esters according to the invention have excellent emulsifying properties.

A further advantage of the present invention is that the formulation comprising the polyglycerol partial esters according to the invention are stable at high temperature. Yet a further advantage of the present invention is that the polyglycerol partial esters according to the invention have a viscosity increasing effect in formulations.

Yet a further advantage of the present invention is that the polyglycerol partial esters according to the invention have an enhanced deposition in the presence of an anionic surfactant Another advantage is, that the polyglycerol partial esters according to the invention are biodegradable and have a low human and environmental toxicity.

Yet another advantage is that the polyglycerol partial esters according to the invention are stable at neutral pH allowing for formulation with material that are not stable at low pH such as enzymes and certain perfumes.

Another advantage is that the polyglycerol partial esters according to the invention provide improved static control over other non-ionic softeners.

DETAILED DESCRIPTION OF THE INVENTION

The person skilled in the art will acknowledge that polyglycerol esters due to their polymeric nature and due to the methods they are prepared by are statistical mixtures of different structures.

Thus, a polyglycerol molecule may comprise ether bonds between two primary positions, a primary and a secondary position, or two secondary positions of the glycerol monomer units. Cyclic structures comprising one or more cycles may also be present. For tetraglycerol and higher oligomers, branched structures comprising at least one glycerol monomer unit linked to three further glycerol monomer units via an ether linkage may be present. A polyglycerol mixture may contain different oligomers and isomers of these, and may be characterized by the oligomer distribution, i.e. the proportion of mono-, di-, tri-, ... -glycerol structures in the mixture. This distribution can for example be determined by high temperature gas chromatography of the polyglycerol mixture after derivatization. Synthesis of single oligoglycerol isomers is described in "Original synthesis of linear, branched and cyclic oligoglycerol standards", Cassel et al., Eur. J. Org. Chem. 2001, 875-896.

Additionally, the esterification of polyglycerol mixtures typically results in a distribution of non-esterified polyglycerol, monoester, diester, triester, etc., where the average degree of esterification is determined by the ratio of fatty acid (or its derivative) to polyglycerol used in the synthesis. If a mixture of different fatty acids is used for the esterification, more than one equal or different fatty acid residues may be linked to one polyglycerol molecule via ester linkage.

For the present invention it is essential that the polyglycerol backbone of the polyglycerol partial ester comprises an average degree of polymerization of from 2 to 8, preferred from 2.5-6, particularly preferred from about 3 to 5.

A suitable method for determining the mean degree of polymerization of the polyglycerol in a given polyglycerol partial ester comprises hydrolysis or alcoholysis of the partial ester, separation of the resulting polyglycerol from the formed carboxylic acid compounds, and analysis by gas chromatography (GC) after derivatization. The GC method also allows differentiating cyclic from non-cyclic structures for oligomers with up to four monomer units (i.e. glycerol to tetraglycerols).

For the calculation of the polydispersity index described below, cyclic and linear structures are added, e.g. the proportion of diglycerol in a mixture consists of the proportion of linear and cyclic diglycerol structures.

For this purpose, the 0.6 g polyglycerol ester is refluxed in 25 ml of 0.5 N ethanolic KOH for 30 minutes and adjusted to pH 2-3 with sulphuric acid. The fatty acids are separated by threefold extraction with an equivalent volume of petroleum ether. The combined extracts are evaporated to a volume of approx. 10 ml. A 0.5 ml aliquot is transferred to an autosampler vial and analyzed by GC after addition of 0.5 ml MTBE and 1 ml TMPAH solution (trimethylanilinium hydroxide in mehanol) as derivatization agent.

Fatty acid GC-analysis is carried out with a gas-chromatograph equipped with split/splitless injector, capillary column and a flame ionisation detector.
Conditions:
injector 290° C., Split 30 ml
Injection volume: 1 μl
column: 30 m*0.32 mm HP1 0.25 μm
  carrier gas helium, head pressure 70 kPa
  temp. prog. 80° C.–300° C. with 8° C./min;
    (conditioning)
detector: FID at 320° C.
  hydrogen 35 ml/min
  air 240 ml/min
  make up gas 35 ml/min
  Applying these conditions the fatty acids methyl esters are separated according to their alkyl chain length.

The relative content of the individual fatty acids (chain length distribution) is evaluated by peak area percentage. The residue after extraction with petroleum ether is adjusted to pH 7-8 by addition of barium hydroxide solution. The precipitate of barium sulphate is separated by centrifugation. The supernatant is removed and the residue extracted thrice with 20 ml of ethanol. The combined supernatants are evaporated at 80° C./50 mbar. The residue is dissolved in pyridine. 500 μl of the solution are transferred to an autosampler vial and 1 ml of MSTFA (N-Methyl-N-trifluoroacetamide) is added. The vial is closed and heated to 80° C. for 30 minutes.

GC-analysis of the polyglycerol component (as its trimethylsilyl derivative) is carried out with a gas-liquid chromatograph equipped with a on column injector and FID detector.
Conditions:
Injector: on column, oven tray
Injection volume: 0.1 μl
Carrier gas: 3 ml/min Hydrogen (constant flow)
Column SimDist 12 m×0.32 mm×0.1 μm (Varian)
Temperature program: 65° C.–365° C., 10° C./min
Detector (FID): 375° C.

Under these conditions, polyglycerols are separated according to their degree of polymerization. Additionally, cyclic isomers are separated from linear ones up to a degree of polymerization of four.

The peak areas of the individual oligomers are separated by a perpendicular applied at the lowest point of the peak valley in between.

Since the resolution of oligomers higher than hexaglycerol is poor, peaks of heptaglycerol and higher oligomers are summarized as "heptaglycerol and higher" and treated as heptaglycerol for the purpose of polydispersity index calculation. Also, for the calculation of the polydispersity index linear and cyclic isomers are summarized.

The relative ratio of the individual polyglycerol oligomers and isomers is calculated from the peak area of the GC obtained as described.

Of course, the described GC analyses of the fatty acid component and polyglycerol component can also be performed on the raw materials which had been used for the preparation of the polyglycerol esters according to the invention.

For the present invention it is essential that polyglycerol obtained by hydrolysis or alcoholysis of the polyglycerol partial ester according to the invention comprises a polydispersity index of greater than 0.75, preferably greater than 1.0, more preferably greater than 1.5.

For the purpose of the present invention, the polydispersity index is calculated as $$\sum_i |n_i - \langle n \rangle| \cdot x_i,$$

where $n_i$ is the degree of polymerization of the single oligomer i, $\langle n \rangle$ is the average degree of polymerization of the polyglycerol mixture, and $x_i$ is the proportion of the oligomer i in the polyglycerol mixture as determined by the GC method described above. For this calculation, the average degree of polymerization $\langle n \rangle$ is calculated from the hydroxyl value (OHV, in mg KOH/g) according to the formula $\langle n \rangle = (112200-18*OHV)/(74*OHV-56100)$.

Polyglycerol depending on its way of preparation can comprise different percentages of cyclic structures. An overview of some cyclic structures present in commercial polyglycerol mixtures is given in "Original synthesis of linear, branched and cyclic oligoglycerol standards", Cassel et al., Eur. J. Org. Chem. 2001, 875-896. For the polyglycerol partial esters according to the present invention it is advantageous if the polyglycerol in the polyglycerol backbone of the partial ester comprises at least 1%, preferably at least 2% and even more preferred at least 3% cyclic structures.

The given percentages are neither percentages by weight nor per mole but are determined by the GC method described above and base on the amount of all polyglycerol.

The radicals $R^5$ in the polyglycerol partial ester might be the same or different within one molecule, preferably they are different.

It is obvious, that the residue $—OR^4$ is determined by the monocarboxylic acid $HOR^4$ used in the esterification reaction for preparing the polyglycerol partial ester. Preferred residues $—OR^4$ are accordingly derived from the acids selected from the group consisting of palmitic acid, stearic acid, arachidic acid, and behenic acid. Mixtures of different acids can be used, too, especially technical mixtures like for example fully or partially hydrogenated palm fatty acids, palm kernel fatty acids, coconut fatty acids, soybean fatty acids, tallow fatty acids, rapeseed fatty acids, high erucic rapeseed fatty acids or distilled fractions of these as long as their iodine value is smaller than 50, preferred smaller than 30 and more preferred smaller than 25. Depending on the degree of hydrogenation and the raw material, these technical mixtures can contain certain amounts of unsaturated fatty acids which then are contained in the polyglycerol partial ester according to the invention. Typical examples of these unsaturated fatty acids are palmitoleic acid, oleic acid, elaidic acid, erucic acid, linoleic acid, and linolenic acid, where oleic acid and elaidic acid are most commonly found as constituents of partially hydrogenated fatty acid mixtures.

The amount of this byproduct can be determined by the iodine value of the fatty acids obtained from the acyl radical by saponification of the polyglycerol partial ester. It is essential to the polyglycerol partial ester of the present invention, that this iodine value is smaller than 50, more preferred smaller than 30 and even more preferred from 1 to 25.

The iodine value can be determined by DIN 53241-1:1995-05.

Preferred polyglycerol partial esters according to the present invention comprise a hydrophilic-lipophilic balance value (HLB value) of between 2 and 10, preferably of between 2.5 to 8, more preferably of between 3 to 6. The HLB value is a measure of the degree to which the molecule is hydrophilic or lipophilic, determined by calculating values for the different regions of the molecule. For the purpose of the present invention, the HLB value of the polyglycerol partial esters is calculated as follows:

$$HLB=(mp/(mp+ma))*20,$$

where mp is the mass of polyglycerol, and ma is the mass of carboxylic acid mixture used in the synthesis of the polyglycerol ester. For example, esterification of 100 g polyglycerol with 100 g fatty acids would result in an HLB of (100 g/(100 g+100 g))*20=10, independent of the degree of polymerization of the polyglycerol and the type of carboxylic acids used.

Preferred polyglycerol partial ester according to the invention are characterized in that they have a melting point of at least 25° C., preferably of at least 35° C., more preferably of at least 40° C. and even more preferably of from 40° C. to 75° C.

The partial esters according to the present invention are obtainable by a process of esterification of a) a polyglycerol mixture comprising an average degree of polymerization of from 2 to 8, preferred from 2.5-6, particularly preferred from about 3 to 5, and a polydispersity index of greater than 0.75, preferably greater than 1.0, more preferably greater than 1.5, with b) at least one monocarboxylic acid comprising a carboxylic acid $HOR^4$, with $R^4$ a linear, unsubstituted acyl radical with a chain length of from 16 to 22 carbon atoms with the proviso that the at least one carboxylic acid bears an iodine value of smaller than 50, preferred smaller than 30, more preferred about 1-25.

It may be beneficial to apply a catalyst (e.g. hydroxides or carbonates of alkali metals; hydroxides of alkaline earth metals; sulfonic acid catalysts like p-toluenesulfonic acid, methanesulfonic acid, trifluoromethanesulfonic acid; metal oxides like zinc(II) oxide or tin(II) oxide) in the esterification process, however the reaction may be performed without addition of a catalyst. The esterification reaction is typically performed at temperatures between 160 and 270° C., preferably between 180 and 250° C. A suitable pressure range for the reaction is from about 50 mbar to about 1200 mbar, preferably from about 600 mbar to ambient pressure. The lower applicable pressure is limited by loss of carboxylic acids from the reaction mixture by distillation.

The iodine value and the mean degree of polymerization can be determined as described above.

It is obvious that instead of the monocarboxylic acids b) suitable derivatives like their anhydrides, their halogenides and their esters, preferably their esters with short chain alcohols like methanol or ethanol, may be used to obtain the polyglycerol partial esters according to the invention.

Preferred polyglycerols used in the process for obtaining the polyglycerol partial ester according to the present invention comprise an average degree of polymerization of 2.5 to 6, particularly preferably of 3 to 4.5.

Particularly preferred polyglycerols used in the process for obtaining the polyglycerol partial ester according to the present invention are selected from the group consisting of polyglycerols with when the degree of polymerization is in the range of 2.5-2.75, then the amount of diglycerol is larger than 40 wt. % and the amount of pentaglycerol and bigger oligomers is larger than 7 wt. %, when the degree of polymerization is in the range 2.75-3.25, then the amount of diglycerol is larger than 35 wt. % and the amount of pentaglycerol and bigger oligomers is larger than 10 wt. %, when the degree of polymerization is in the range of 3.25-3.75, then the amount of diglycerol is larger than 30 wt. % and the amount of pentaglycerol and bigger oligomers is larger than 15 wt. %, when the degree of polymerization is in the range of 3.75-4.5, then the amount of diglycerol is larger than 25 wt. % and the amount of pentaglycerol and bigger oligomers is larger than 20 wt. % and when the degree of polymerization is in the range of 4.5-6.0, then the amount of diglycerol is larger than 20 wt. % and the amount of pentaglycerol and bigger oligomers is larger than 30 wt. %, whereby the wt. % refer to the total amount of polyglycerol.

The polyglycerol used in the esterification process described above can be produced by several methods.

Suitable methods for the production of polyglycerol include polymerization of glycidol (e.g. with base catalysis), polymerization of epichlorohydrin (e.g. in the presence of equimolar amounts of a base like NaOH), or polycondensation of glycerol.

The preferred method for the purpose of this invention is condensation of glycerol, in particular in the presence of catalytic amounts of base, preferably NaOH or KOH. Suitable reaction conditions include temperatures of 220-260° C. and reduced pressure (20-800 mbar, preferably 50-500 mbar) to facilitate removal of reaction water from the mixture. The progress of the condensation reaction may be followed by measuring refractive index, viscosity, or hydroxyl value of the reaction product.

A particularly preferred method, which results in a desired broader polydispersity of the product, comprises the steps of
  reacting glycerol in a condensation reaction in the presence of a catalytic amount (0.2-5% by weight) of base at a temperature from about 220-260° C. at a pressure between 250 and 1000 mbar while removing reaction water by distillation until the reaction mixture contains less than 70% (preferably less than 60%) of glycerol
  continuing the condensation reaction at a lower pressure between 20 and 200 mbar while removing reaction water and glycerol by distillation until the hydroxyl value of the reaction mixture is lower than 1400 (preferably lower than 1200), and
  optionally neutralizing the catalyst with an acid.

The iodine value and the polydispersity index can be determines as described above.

A preferred method for preparation of the polyglycerol partial esters according to the invention makes use of the proviso that the ratio by weight of polyglycerol mixture to monocarboxylic acid is in the range from 0.11 to 1, preferably in the range from 0.11 to 0.67.

As the polyglycerol partial esters according to the invention are more easily to handle when being dissolved in a solvent a further part of the invention is a polyglycerol partial ester concentrate wherein a solvent is present consisting of
A) at least 50 wt. %, preferably at least 60 wt. %, even more preferably at least 70 wt. % of at least one polyglycerol partial esters according to the invention,
B) up to 50 wt. % of the solvent and optionally
C) 0.1 wt. % to 5 wt. % of a preservative,
wherein the wt. % refer to the total weight of the concentrate and the wt. % of all components sum up to 100 wt. %.

Preferably the solvent is present in an amount of 0.1 wt. % to 50 wt. %, more preferably in an amount of 5 wt. % to 50 wt. %

Suitable solvents are ethanol, isopropanol, propylenglycol, 1,3-propandiol, butylenglycol, pentylenglycol, natural oils like coconut oil, rapeseed oil and the like.

EXAMPLES

To show the superior performance of the polyglycerol partial ester according to the present invention the following tests were applied to determine the extraction energy reduction (EER) capabilities:

The polyglycerol partial ester according to the present invention are first emulsified to obtain an ending concentration of 25 wt. % PGE, 5 wt. % cetyl trimethylammonumchloride (CTMAC) and 3.2 wt. % Tergitol TMN-6 (nonionic surfactant available from Dow Chemical). If necessary the PGE raw material was heated until just above its melting point then mixed with the TMN-6 and stirred until evenly mixed. This mixture was then added slowly to a heated (melting temp of PGE) container containing CTMAC and mixed with an overhead mixer (IKA Labortechnik, model # RWZODZM-N) at 1500 rpm until all of the PGE/TMN-6 is added and a creamy white emulsion was obtained. Deionized water was added slowly to the mixture while being stirred at 1500 rpm to obtain the desired end concentration. The mixture was cooled in an ice bath to room temperature.

The fabric used for the present method was a 13 inch×13 inch white terry cloth, manufactured by Standard Textile. The brand name is Eurotouch and it is composed of 100% cotton. The universal product number is 63491624859. The correspondence address for Standard Textile is One Knollcrest Drive, Cincinnati, Ohio 45237.

To perform a standard forced deposition terry coating method the PGE emulsion described above was diluted to the appropriate concentration (0.3% based on weight) with deionized water. The dilute PGE emulsion was added to a 13"×15" glass cake pan so that it is 1× the weight of the terry being used (~55g depending on terry). The container used to measure the PGE emulsion was rinsed with an equal amount of deionized water, this rinse was added to the same cake pan. The cake pan was agitated until the solution appeared homogenous. The terry tag side was laid down flat into the cake pan. The edges that did not fit into the pan were folded toward the center of the terry. The terry was bunched up and squeezed with both hands,—distributing the material evenly onto the terry. All excess material in the cake pan was soaked up with the terry. The fabrics were tumble dried for 55 min on cotton/high setting/timed dry with a Kenmore 80 Series Dryer, Model 110.64832400. The cake pan was washed between samples with an alcohol wipe.

The control samples were prepared accordingly but instead of the PGE emulsions plain deionized water was used. Phabrometer measurement procedures were carried out as follows:

The following measurement procedures are for the Phabrometer Fabric Evaluation System FES-2, manufactured by Nu Cybertek, Inc, Davis, California. Instrument—Phabrometer Fabric Evaluation System, FES-2 with fabric evaluation software version 1.1.3.

The circular weight that compresses the terry during phabrometer operation had a mass of 1466 grams. The weight comprises of two identical halves, each weighing 733 grams. The terry was pushed through a ring that has an inside diameter of 37.93 mm. Both the weight and the ring were purchased from Nu Cybertek.

Prior to measurement, fabrics were cut with a dye into circles that have a diameter of 11.0 cm. Fabrics had to equilibrate in a constant temperature (CT) room for 24 hours before measuring. The CT room temperature is 70° F. with a relative humidity of 50%. Between each fabric measurement, the bottom of the weight, the inside of the ring, and the base in which the ring is sitting were cleaned with an alcohol wipe having 70% isopropyl alcohol and 30% deionized water. Alcohol wipes were purchased from VWR International. The address for VWR is 1310 Goshen Parkway, West Chester, Pa. 19380. The catalog number is 21910-110. The weight and ring were allowed to dry completely before the next measurement. Once used, a fabric swatch cannot be re-measured.

For data analysis all raw data was exported to Microsoft Excel 2007. There are 108 data points in each exported curve, but only the first 100 are used. Each curve is integrated from 1 to 100 and the sum is reported as the unitless "Extraction Energy". For each test treatment a minimum of 6 fabric replicates are evaluated (sampling from as many different terry cloths as possible) and a sample Standard Deviation is calculated. "Extraction Energy Reduction" (EER) is obtained by subtraction of the average extraction energy of the control samples (minimum of 6) from the extraction energy average of the fabric samples treated with the above disclosed polyglycerol materials (minimum of 6 per each treatment).

The higher the EER value the softer the fabric. A value of from about 7 to 9 represents a weak softening effect. According to the above-mentioned procedure a typical fabric softener like Downy reaches an EER value of about 15.

Comparative Example 1

PGE 3 (Low Polydispersity Index)

The PGE of comparative example 1 ("Compare 1") comprises a polyglycerol with a low polydispersity index and was prepared as follows:

500 g glycerol and 2.5 g of potassium hydroxide were heated to 240° C. at a pressure of 400 mbar while nitrogen was bubbled through the mixture. Reaction water was continuously distilled from the reaction mixture. When the refractive index reached 1.4920, the reaction mixture was cooled and subjected to thin film distillation at a temperature of 250° C. and a pressure of 4 mbar.

The distillation residue had a hydroxyl value of 1150 mg KOH/g, a polydispersity index of 0.71 and contained 1.5% of cyclic polyglycerols.

240 g of this product were reacted with 551.6 g of partially hydrogenated tallow fatty acid (C16/18) with an iodine value of 20 at a temperature of 240° C. while sparging with nitrogen. Reaction water was continuously distilled from the mixture. When the acid value reached <1 mg KOH/g, the reaction was stopped by cooling.
Hydroxyl value: 216 mg KOH/g
Acid value: 0.4 mg KOH/g
Saponification value: 149 mg KOH/g
HLB (calculated): 6.1
EER 11.6

Comparative Example 2

PGE 31 (Low Polydispersity Index)

The PGE of comparative example 2 ("Compare 2") comprises a polyglycerol with a low polydispersity index and was prepared as follows:

240 g of commercial triglycerol (polydispersity index 0.17) were reacted with 551.6 g of partially hydrogenated tallow fatty acid (C16/18) with an iodine value of 20 at a temperature of 240° C. while sparging with nitrogen.

Reaction water was continuously distilled from the mixture. When the acid value reached <1 mg KOH/g, the reaction was stopped by cooling.
Hydroxyl value: 243 mg KOH/g
Acid value: 0.6 mg KOH/g
Saponification value: 129 mg KOH/g
HLB (calculated): 6.1
EER 10.3

Example 1

PGE 24

500 g glycerol and 2.5 g of potassium hydroxide were heated to 240° C. at a pressure of 400 mbar while sparging with nitrogen. Reaction water was continuously distilled from the reaction mixture. When the refractive index reached 1.4910 the reaction was stopped by cooling The product had a hydroxyl value of 1170 mg KOH/g, a polydispersity index of 1.33, and contained 5.5% of cyclic polyglycerols.

240 g of this product were reacted with 551.6 g of partially hydrogenated tallow fatty acid (C16/18) with an iodine value of 20 at a temperature of 240° C. while sparging with nitrogen. Reaction water was continuously distilled from the mixture. When the acid value reached <1 mg KOH/g, the reaction was stopped by cooling.
Hydroxyl value: 210 mg KOH/g
Acid value: 1.1 mg KOH/g
Saponification value: 153 mg KOH/g
HLB (calculated): 6.1
EER 17.1

Example 2

PGE 25

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

240 g of this product were reacted with 275.8 g of partially hydrogenated tallow fatty acid (C16/18) with an iodine value of 20 at a temperature of 240° C. while sparging with nitrogen. Reaction water was continuously distilled from the mixture. When the acid value reached <1 mg KOH/g, the reaction was stopped by cooling.
Hydroxyl value: 191 mg KOH/g
Acid value: 0.1 mg KOH/g
Saponification value: 156 mg KOH/g
HLB (calculated): 9.8
EER 15.9

The following table shows the superior performance of the polyglycerol partial esters according to the present invention in the test methods described above. It is obvious, that the correct polydispersity index of the polyglycerol component is of uttermost importance for the PGE to be useful as fabric softening agent.

| PGE | comment | EER |
| --- | --- | --- |
| Compare 1 | low polydispersity | 11.6 |
| Compare 2 | low polydispersity | 10.3 |
| Example 1 |  | 17.1 |
| Example 2 |  | 15.9 |

Comparative Example 3

PGE 20

The PGE of comparative example 3 ("Compare 3") comprises an $R^4$ acyl radical with less than 16 carbon atoms and was prepared as follows:

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

282 g of this product [polyglycerol] were reacted with 518 g of hardened, topped coconut oil fatty acid (C12-18) at a temperature of 240° C. while sparging with nitrogen.

Reaction water was continuously distilled from the mixture. When the acid value reached <2 mg KOH/g, the reaction was stopped by cooling.
Hydroxyl value: 241 mg KOH/g
Acid value: 1.1 mg KOH/g
Saponification value: 177 mg KOH/g
HLB (calculated): 7.0
EER 3.4

Comparative Example 4

PGE 21

The PGE of comparative example 4 ("Compare 4") comprises a branched $R^4$ acyl radical and was prepared as follows:

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

234.2 g of this product were reacted with 565.8 g of isostearic acid (Emersol 847, Cognis) at a temperature of 240° C. while sparging with nitrogen. Reaction water was continuously distilled from the mixture. When the acid value reached <1 mg KOH/g, the reaction was stopped by cooling.
Hydroxyl value: 182 mg KOH/g
Acid value: 0.5 mg KOH/g
Saponification value: 149 mg KOH/g
HLB (calculated): 5.9
EER 5.4

Comparative Example 5

PGE 22

The PGE of comparative example 5 ("Compare 5") comprises an unsaturated $R^4$ acyl radical with a high IV and was prepared as follows:

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

243 g of this product were reacted with 567 g of commercial 70+% oleic acid (iodine value 95 mg KOH/g) at a temperature of 240° C. while sparging with nitrogen. Reaction water was continuously distilled from the mixture. When the acid value reached <1 mg KOH/g, the reaction was stopped by cooling.
Hydroxyl value: 193 mg KOH/g
Acid value: 0.6 mg KOH/g
Saponification value: 149 mg KOH/g
HLB (calculated): 6.0
EER 2.4

Comparative Example 6

PGE 23

The PGE of comparative example 6 ("Compare 6") comprises an hydroxyl-substituted $R^4$ acyl radical and was prepared as follows:

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

233.3 g of this product were reacted with 576.7 g of 12-hydroxystearic acid at a temperature of 240° C. while sparging with nitrogen. Reaction water was continuously distilled from the mixture. When the acid value reached <1 mg KOH/g, the reaction was stopped by cooling.
Hydroxyl value: 300 mg KOH/g
Acid value: 0.3 mg KOH/g
Saponification value: 134 mg KOH/g
HLB (calculated): 5.6
EER 8.3

Example 3

PGE 17

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

254.8 g of this product were reacted with 545.2 g of palmitic acid (C16) at a temperature of 240° C. while sparging with nitrogen. Reaction water was continuously distilled from the mixture. When the acid value reached <1 mg KOH/g, the reaction was stopped by cooling.
Hydroxyl value: 209 mg KOH/g
Acid value: 0.6 mg KOH/g
Saponification value: 160 mg KOH/g
HLB (calculated): 6.4
EER 14.7

Example 4

PGE 18

500 g glycerol and 2.5 g of potassium hydroxide were heated to 240° C. at a pressure of 400 mbar while sparging with nitrogen. Reaction water was continuously distilled from the reaction mixture. When the refractive index reached 1.4840, the pressure was lowered to 50 mbar and the condensation reaction was continued for 1.5 h while glycerol was distilled from the product.

The product had a hydroxyl value of 1156 mg KOH/g, a polydispersity index of 1.17, and contained 5.2% of cyclic polyglycerols.

236.3 g of this product were reacted with 563.7 g of stearic acid (C18) at a temperature of 240° C. while sparging with nitrogen. Reaction water was continuously distilled from the mixture. When the acid value reached <1 mg KOH/g, the reaction was stopped by cooling.
Hydroxyl value: 194 mg KOH/g
Acid value: 0.6 mg KOH/g
Saponification value: 147 mg KOH/g
HLB (calculated): 5.9
EER 16.6

The following table shows the superior performance of the polyglycerol partial esters according to the present invention in the test methods described above. It is obvious, that it is of uttermost importance for the PGE to comprise unsubstituted, unbranched $R^4$ acyl radicals with 16 to 22 carbon atoms and an IV smaller than 50 to be useful as fabric softening agent.

| PGE | comment | EER |
|---|---|---|
| Compare 3 | short $R^4$ | 3.4 |
| Compare 4 | branched $R^4$ | 5.4 |
| Compare 5 | unsaturated $R^4$ | 2.4 |
| Compare 6 | substituted $R^4$ | 8.3 |
| Example 2 | | 15.9 |
| Example 3 | | 14.7 |
| Example 4 | | 16.6 |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

The invention claimed is:

1. A polyglycerol partial ester having the structure of Formula (I)

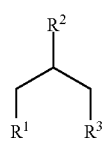

Formula (I)

wherein $R^1$, $R^2$ and $R^3$, independent from each other, equal or different, are selected from the group consisting of:
—OH,
—$OR^4$, where $R^4$ is a linear, unsubstituted acyl radical with a chain length of from 16 to 22 carbon atoms with the proviso that the monocarboxylic acids obtained from the acyl radical by saponification bears an iodine value of smaller than 50, and
—$OR^5$, where $R^5$ is a radical having the structure of Formula (I) wherein one of $R^1$, $R^2$ and $R^3$ being a direct bond to the oxygen of —$OR^5$
wherein each molecule of the polyglycerol partial ester comprises at least one of each —$OR^4$ and —$OR^5$, with the provisos that the polyglycerol obtained by hydrolysis or alcoholysis of the polyglycerol partial ester comprises an average degree of polymerization of from 2 to 8 and the polydispersity index of said polyglycerol is greater than 0.75, wherein said polydispersity index is calculated as $$\sum_i |n_i - \langle n \rangle| \cdot x_i,$$

where $n_i$, is the degree of polymerization of a single oligomer i, $\langle n \rangle$ is an average degree of polymerization of a polyglycerol mixture, and $x_i$, is a proportion of the single oligomer i in the polyglycerol mixture.

2. The polyglycerol partial ester according to claim 1 wherein at least 1% of the polyglycerol obtained by hydrolysis or alcoholysis of the polyglycerol partial ester comprises cyclic structures.

3. The polyglycerol partial ester according to claim 1, wherein the polyglycerol partial ester comprises an HLB-value from 2 to 10.

4. The polyglycerol partial ester according to claim 1, wherein said polyglycerol partial ester has a melting point of at least 25° C.

5. A method for the preparation of polyglycerol partial esters comprising the process of esterification of:

a) a polyglycerol mixture comprising an average degree of polymerization of from 2 to 8 with b) at least one monocarboxylic acid comprising a carboxylic acid $HOR^4$, with $R^4$ a linear, unsubstituted acyl radical with a chain length of from 16 to 22 carbon atoms with the proviso that the at least one carboxylic acid bears an iodine value of smaller than 50, said polyglycerol partial esters having the structure of Formula (I)

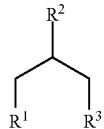

Formula (I)

wherein $R^1$, $R^2$ and $R^3$, independent from each other, equal or different, are selected from the group consisting of:
—OH, —$OR^4$, where $R^4$ is a linear, unsubstituted acyl radical with a chain length of from 16 to 22 carbon atoms with the proviso that the monocarboxylic acids obtained from the acyl radical by saponification bears an iodine value of smaller than 50, and
—$OR^5$, where $R^5$ is a radical having the structure of Formula (I) wherein one of $R^1$, $R^2$ and $R^3$ being a direct bond to the oxygen of —$OR^5$
wherein each molecule of the polyglycerol partial ester comprises at least one of each —$OR^4$ and —$OR^5$, with the provisos that the polyglycerol obtained by hydrolysis or alcoholysis of the polyglycerol partial ester comprises an average degree of polymerization of from 2 to 8 and the polydispersity index of said polyglycerol is greater than 0.75, wherein said polydispersity index is calculated as $$\sum_i |n_i - \langle n \rangle| \cdot x_i,$$

where $n_i$, is the degree of polymerization of a single oligomer i, $\langle n \rangle$ is an average degree of polymerization of a polyglycerol mixture, and $x_i$, is a proportion of the single oligomer i in the polyglycerol mixture.

6. A polyglycerol partial ester concentrate wherein a solvent is present consisting of
A) at least 50 wt. % of at least one polyglycerol partial esters according to claim 1,
B) up to 50 wt. % of a solvent and optionally
C) 0.1 wt. % to 5 wt. % of a preservative,
wherein the wt. % refer to the total weight of the concentrate and the wt. % of all components sum up to 100 wt. %.

* * * * *